(12) United States Patent
Kandala

(10) Patent No.: US 8,614,586 B1
(45) Date of Patent: Dec. 24, 2013

(54) METHOD AND APPARATUS FOR MEASURING PEANUT MOISTURE CONTENT

(75) Inventor: Chari Kandala, Athens, GA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 529 days.

(21) Appl. No.: 13/005,168

(22) Filed: Jan. 12, 2011

(51) Int. Cl.
*G01R 27/26* (2006.01)

(52) U.S. Cl.
USPC ........... 324/664; 324/639; 324/694; 324/640; 73/73; 34/560; 34/484

(58) Field of Classification Search
USPC ....................................................... 324/664
See application file for complete search history.

(56) References Cited

U.S. PATENT DOCUMENTS

| | | | |
|---|---|---|---|
| 2,654,054 A | 9/1882 | French | |
| 3,739,266 A * | 6/1973 | Neitzel et al. | 324/667 |
| 4,058,766 A * | 11/1977 | Vogel et al. | 324/667 |
| 4,193,116 A * | 3/1980 | Funk | 702/23 |
| 4,326,163 A * | 4/1982 | Brooke | 324/640 |
| 4,408,128 A * | 10/1983 | Fujita | 324/694 |
| 4,599,809 A * | 7/1986 | Parkes | 34/484 |
| 4,991,915 A * | 2/1991 | Thompson et al. | 324/640 |
| 5,039,947 A * | 8/1991 | Kraszewski et al. | 324/634 |
| 5,092,819 A * | 3/1992 | Schroeder et al. | 460/7 |
| 5,144,755 A * | 9/1992 | Braun et al. | 34/560 |
| 5,212,453 A * | 5/1993 | Koehler et al. | 324/664 |
| 5,218,309 A * | 6/1993 | Nelson et al. | 324/664 |
| 5,253,512 A | 10/1993 | Le Gigan | |
| 5,570,521 A * | 11/1996 | Baker et al. | 34/550 |
| 6,204,670 B1 * | 3/2001 | Joshi | 324/643 |
| 6,407,555 B2 * | 6/2002 | Joshi et al. | 324/636 |
| 6,437,582 B1 * | 8/2002 | Rode et al. | 324/664 |
| 6,570,395 B2 * | 5/2003 | Falbo et al. | 324/664 |
| 6,691,563 B1 * | 2/2004 | Trabelsi et al. | 73/73 |
| 6,819,121 B1 * | 11/2004 | Hager et al. | 324/664 |
| 6,904,789 B2 * | 6/2005 | Campbell et al. | 73/73 |
| 6,982,562 B2 * | 1/2006 | Rains et al. | 324/694 |
| 7,151,381 B2 * | 12/2006 | Fraser | 324/664 |
| 7,190,176 B2 * | 3/2007 | France | 324/639 |
| 2003/0015024 A1 * | 1/2003 | Campbell et al. | 73/73 |
| 2004/0100285 A1 * | 5/2004 | Rains et al. | 324/664 |
| 2005/0225334 A1 * | 10/2005 | Rains et al. | 324/694 |

OTHER PUBLICATIONS

Kandala, C.V.K. et al., A Low Cost Impedance Analyzer and Capacitor Sensor for Nondestructive Measurement of Moisture Content of In-Shell Peanuts, Manuscript Agricultural Research Service, U.S. Department of Agriculture, Dawson, GA.

Kandala, C.V. et al., Nondestructive Measurement of Moisture Content Using a Parallel-Plate Capacitance Sensor for Grain and Nuts, IEEE Sensors Journal, 2010, pp. 1-6.

Kandala, C.V.K. et al., Moisture Content Determination for In-Shell Peanuts with a Low-Cost Impedance Analyzer and Capacitor Sensor, American Society of Agricultural and Biological Engineers, 2008, vol. 51(4): 1377-1381.

* cited by examiner

*Primary Examiner* — Patrick Assouad
*Assistant Examiner* — Benjamin M Baldridge
(74) *Attorney, Agent, or Firm* — John Fado; Robert D. Jones; Lesley Shaw

(57) ABSTRACT

The moisture measuring method and apparatus determines the moisture content of post-harvest in-shell peanuts. A crystal oscillator generates a high frequency signal that is directed through a selected sample of in-shell peanuts. Capacitance, impedance, and phase change data associated with the sample are generated at (at least) two frequencies. The data is then substituted into a semi-empirical equation to determine the moisture content of the in-shell peanuts.

23 Claims, 6 Drawing Sheets

METHOD AND APPARATUS FOR MEASURING PEANUT MOISTURE CONTENT

FIELD OF THE INVENTION

The present invention relates to a method and apparatus for measuring the moisture content of nuts. Specifically, the invention relates to a method and apparatus for measuring the moisture content of post-harvest in-shell peanuts.

BACKGROUND OF THE INVENTION

A determination of the moisture content of peanuts is essential to peanut processing. After harvest the peanuts are dried until the moisture content is below 10.5% by weight. Drying the peanuts further adversely affects the flavor and desirability of the nut. Drying also decreases the weight of a farmer's bulk peanut product, thereby correspondingly decreasing the amount that the farmer is paid for the product. However, if peanuts are not sufficiently dried, they are susceptible to infection by the mold fungus *Aspergillus flavus* which releases the toxic substance aflatoxin.

To produce safe, high quality peanuts, the peanut moisture content is tested essentially continually during the drying process. Currently the most conventional method for determining peanut moisture content requires that operators shell approximately 1 kg of peanuts and load the shelled peanuts into laboratory equipment for testing. However, this process is time consuming and inconvenient and, due to the need for continuous testing, eventually wastes a significant amount of the peanut product.

The need exists for a relatively quick, non-destructive, and convenient means of measuring in-shell peanut moisture content. The current invention comprises a mobile method and apparatus that accurately, efficiently, and non-destructively measures the moisture content of in-shell peanuts.

SUMMARY OF THE INVENTION

The current invention is directed to a method and an apparatus for determining the moisture content of a selected sample of in-shell peanuts. At the initiation of the moisture determination process, a sample of in-shell peanuts is loaded into a sample holder. An oscillator in combination with a crystal generates a 5 volt square wave signal. The signal is buffered and directed to a filter which shapes the signal into a sine wave.

The signal is then split into a measurement signal, a reference signal, and a phase detection signal. The reference signal is sent through a transformer and rectifier and then measured. The phase detection signal is sent through an attenuator and into a phase detector.

The measurement signal is sent to a multiplexer and then through the selected sample of in-shell peanuts. The measurement signal is then directed from the multiplexer to a range resistor in combination with an operational amplifier. A first portion of the measurement signal is then rectified and measured. A second portion of the measurement signal is sent to a comparator, which outputs the signal as a square wave. The signal is then directed to a filter and converted into a sine wave. The measurement signal is then directed to the phase detector which measures a phase change between the measurement signal and the phase detection signal.

The moisture content of the in-shell peanut sample is calculated based on measurement of the reference signal, the measurement signal, and the phase change. Specifically, a first data set is generated at a first oscillator frequency, and a second data set is generated at a second oscillator frequency. The measurements in the first and second data sets are converted to values for impedance, capacitance, and phase change—and then the values are substituted into a semi-empirical equation to determine the moisture content of the in-shell peanuts.

DETAILED DESCRIPTION OF PREFERRED EMBODIMENTS

Figure 1:
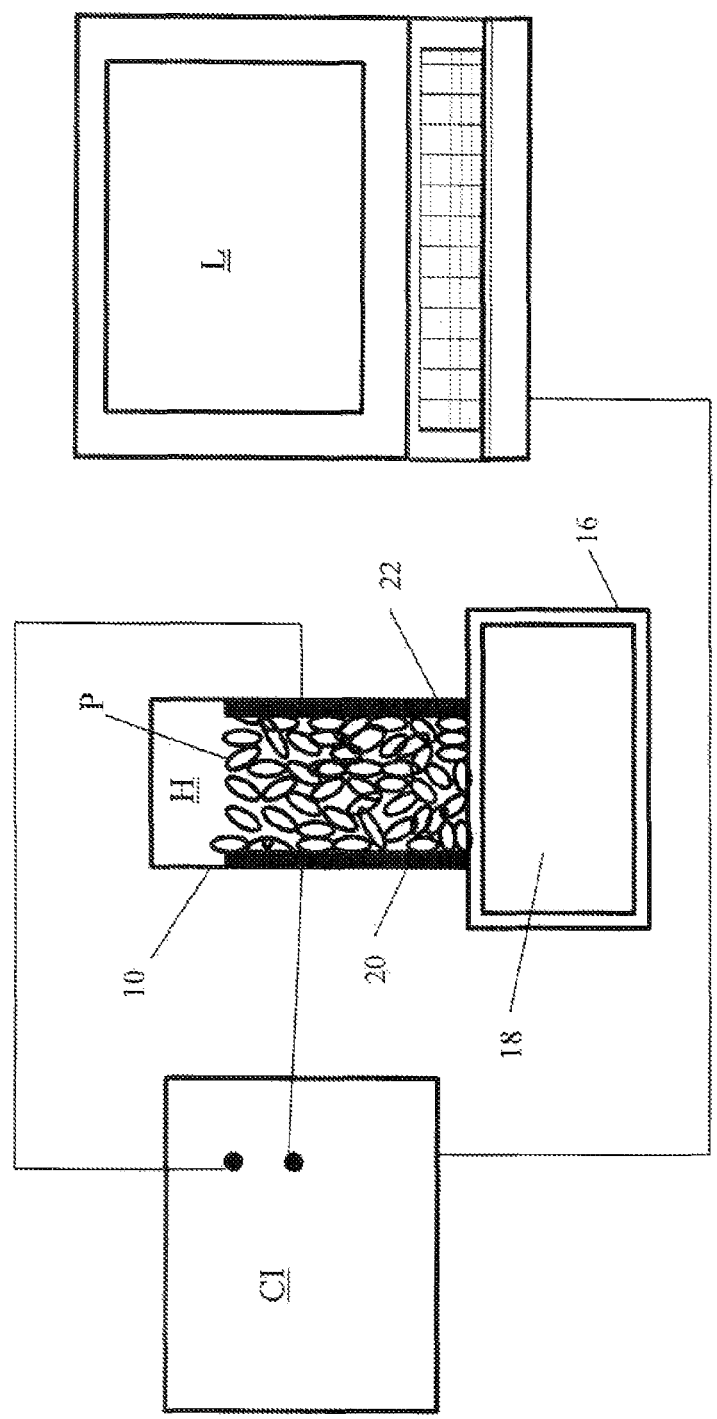
FIG. 1 is a schematic of the moisture measuring apparatus of the current invention.

As generally shown in the FIG. 1 schematic, the current invention comprises a system for measuring the moisture content of peanuts P while the peanuts are still in their shell (i.e. "in-shell peanuts"). The system includes a moisture content analyzer CI, a sample holder H, and a computer L. In the preferred embodiment, data derived from the analyzer CI is processed and displayed on a computer L, preferably on a portable laptop computer screen. The laptop L may also control the functions of the analyzer CI during the measurement process.

As shown in FIG. 1, an upper portion of the sample holder H comprises a hollow acrylic cylinder 10 fitted with a parallel-plate electrode assembly 20, 22. In the preferred embodiment, the cylinder 10 is 190 mm long with an internal diameter of 50 mm and a wall thickness of 7 mm. The electrode assembly comprises two parallel rectangular aluminum plates 20, 22 that are 140 mm long and 50 mm wide. The plates 20, 22 are positioned inside the cylinder 10 approximately 25 mm from the ends of the cylinder 10. The distance between the plates 20, 22 is about 42 mm.

The cylinder 10 rests on top of a rectangular acrylic box 16. The box 16 includes a drawer 18 that slides in and out of an opening in the front side of the box 16. The box 16 is constructed so that when the drawer 18 is closed, the sample peanuts P are supported inside the cylinder 10. However, when the drawer 18 is pulled forward, the cylinder 10 aligns with a hole (not shown) in the top of the box 16 so that the sample peanuts P fall through the cylinder 10 and into a rear portion of the drawer 18.

In operation, the moisture-measuring process is initiated by closing the drawer 18 and filling the cylinder 10 with in-shell peanuts P. The parallel plates 20, 22 are then energized and measurements are obtained. After the measurements are complete, the drawer 18 is moved to the open position so that all peanuts P fall out of the cylinder 10, through the hole in the top of the box 16, and into the drawer 18. The drawer 18 is then removed from the box 16 and the peanuts P in the drawer 18 are deposited back into a source container. The drawer 18 then slides back into the box 16 so that the cylinder 10 can once again be filled with sample peanuts P and the measurement process can be repeated.

Figure 2:
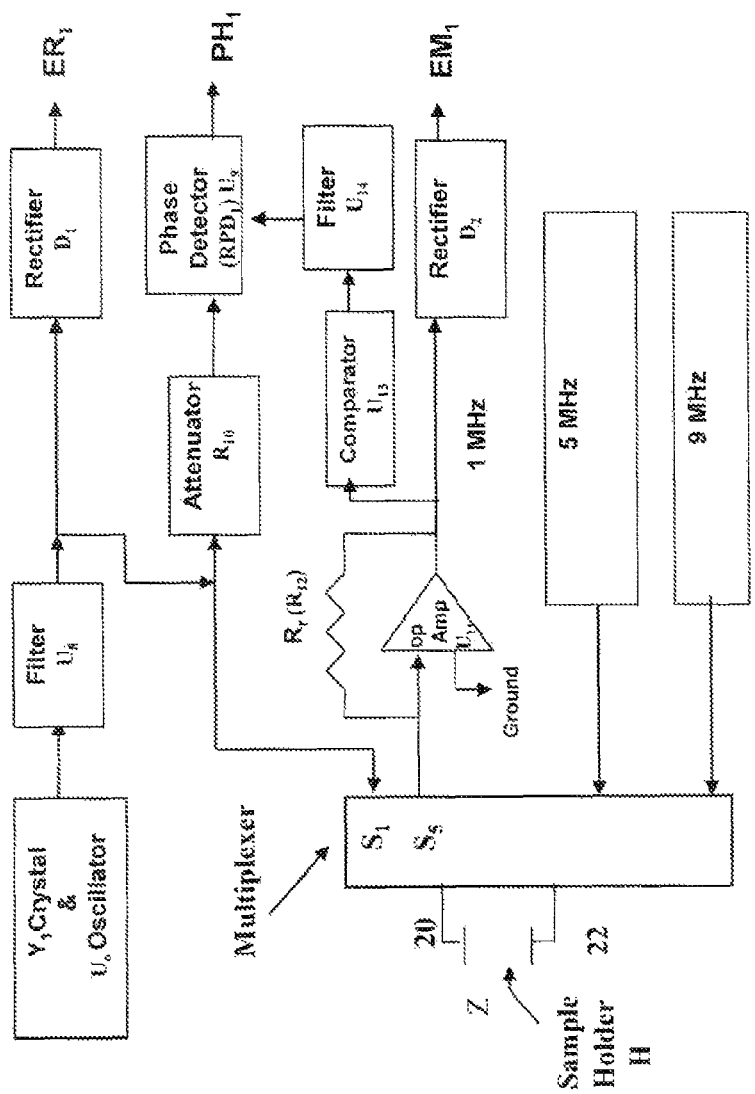
FIG. 2 is a block diagram schematic of the moisture content analyzer of the current invention.

One aspect of the current invention comprises an improved moisture content analyzer CI. The analyzer CI automatically measures selected properties of the peanut sample at three frequencies: 1, 5, and 9 MHz. FIG. 2 shows a block diagram associated with the 1 MHz signal, however the circuitry associated with the 5 and 9 MHz signals is essentially similar. FIGS. 3-6 are circuit diagrams that show the moisture content analyzer CI in greater detail.

Figure 3:
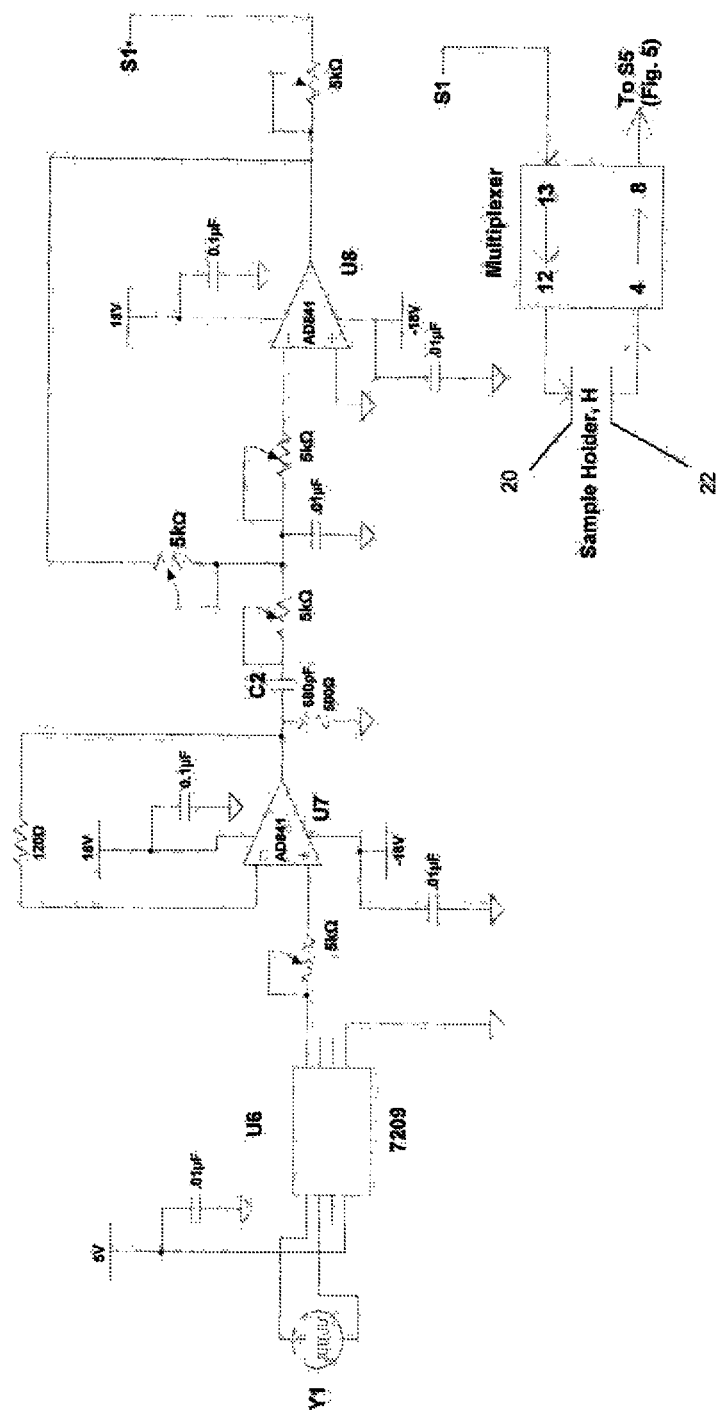
FIG. 3 is a circuit diagram generally associated with the crystal Y1 and oscillator U6.

As best shown in FIGS. 2 and 3, an original signal is generated by a crystal Y1 in combination with an oscillator U6. In the preferred embodiment, the oscillator U6 comprises an ICM 7209 chip. The oscillator U6 generates a 1.0 MHz square wave which has a 5V amplitude. As discussed supra, similar circuits are used to generate 5 and 9 MHz signals.

As shown in FIG. 3, the original signal is then buffered by operational amplifier U7. The signal then flows to operational amplifier U8 which filters and shapes the signal into a sine wave of the same amplitude (i.e. 5V). In the preferred embodiment the U7 and U8 operational amplifiers comprise AD841 amplifiers, which are well-known in the art.

Figure 4:
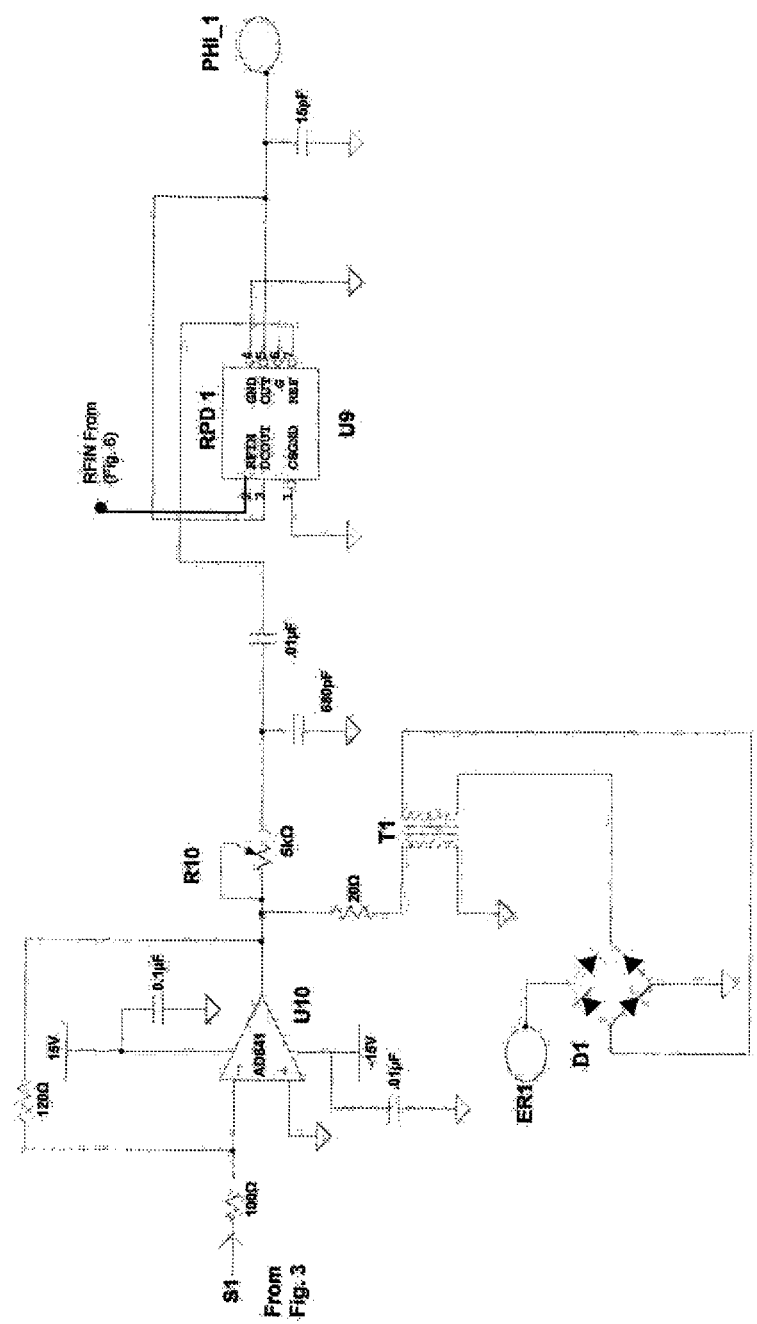
FIG. 4 is a circuit diagram generally associated with the phase detector RPD1 (U9).

As shown in FIGS. 2 and 3, a measurement portion of the original signal is then directed into a multiplexer at S1. As best shown in FIG. 4, another portion of the original signal is sent through an operational amplifier U10 (also an AD841). The original signal is then split into a reference signal and a phase detection signal. The reference signal is directed to an amplitude-measuring system comprising a transformer T1 and a rectifier D1. This reference signal is measured and designated as ER1. The phase detection signal is directed through an attenuator R10 and is fed into a phase detector RPD1 (U9).

As best shown in the lower right portion of FIG. 3, the measurement signal at S1 enters a multiplexer at pin 13 and exits at pin 12. The measurement signal is then directed through an electrode plate 20 and into the sample holder H. After passing through the peanuts P in sample holder H, the measurement signal is received by an electrode plate 22 and directed back into the multiplexer at pin 4 and emerges at pin 8. At S5 the measurement signal is directed away from the multiplexer and into a circuit associated with a comparator U13, as shown in greater detail in FIG. 5

Figure 5:
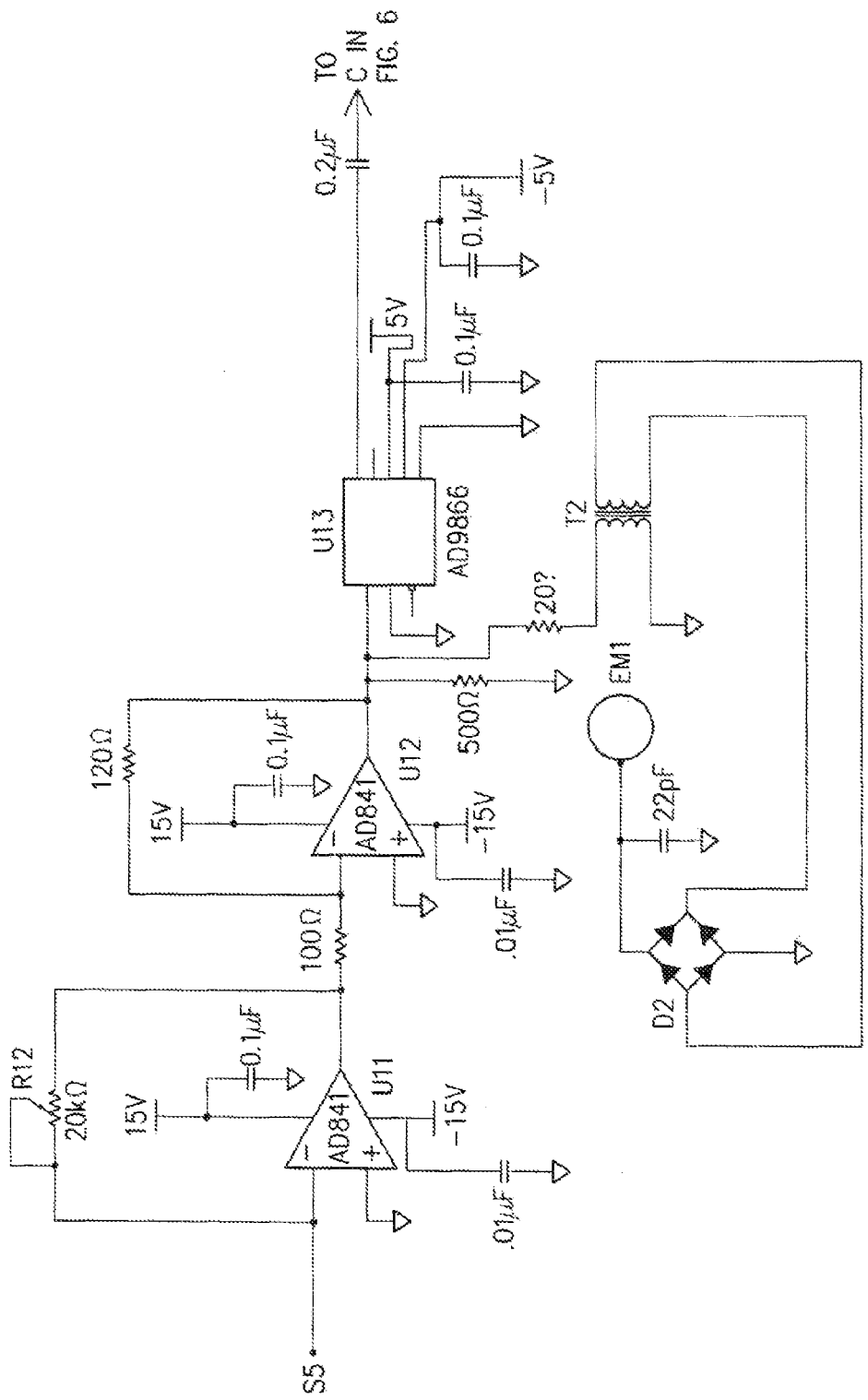
FIG. 5 is a circuit diagram for the circuit generally associated with the comparator U13.

As best shown in FIG. 5, the measurement signal at S5 is directed into an operational amplifier U11 (also an AD841) and through a variable range resistor R12. The signal is then buffered by an operational amplifier U12 (also an AD841). A first portion of the measurement signal is sent through the transformer T2 and then rectified and measured as EM1. The magnitude of the impedance of the in-shell peanut sample at 1 MHz is calculated as $|Z1|=R12 (ER1/EM1)$.

As best shown in FIG. 5, a second portion of the measurement signal is sent to a comparator U13, which outputs the signal as a square wave. In the preferred embodiment, the comparator U13 comprises an AD9866.

Figure 6:
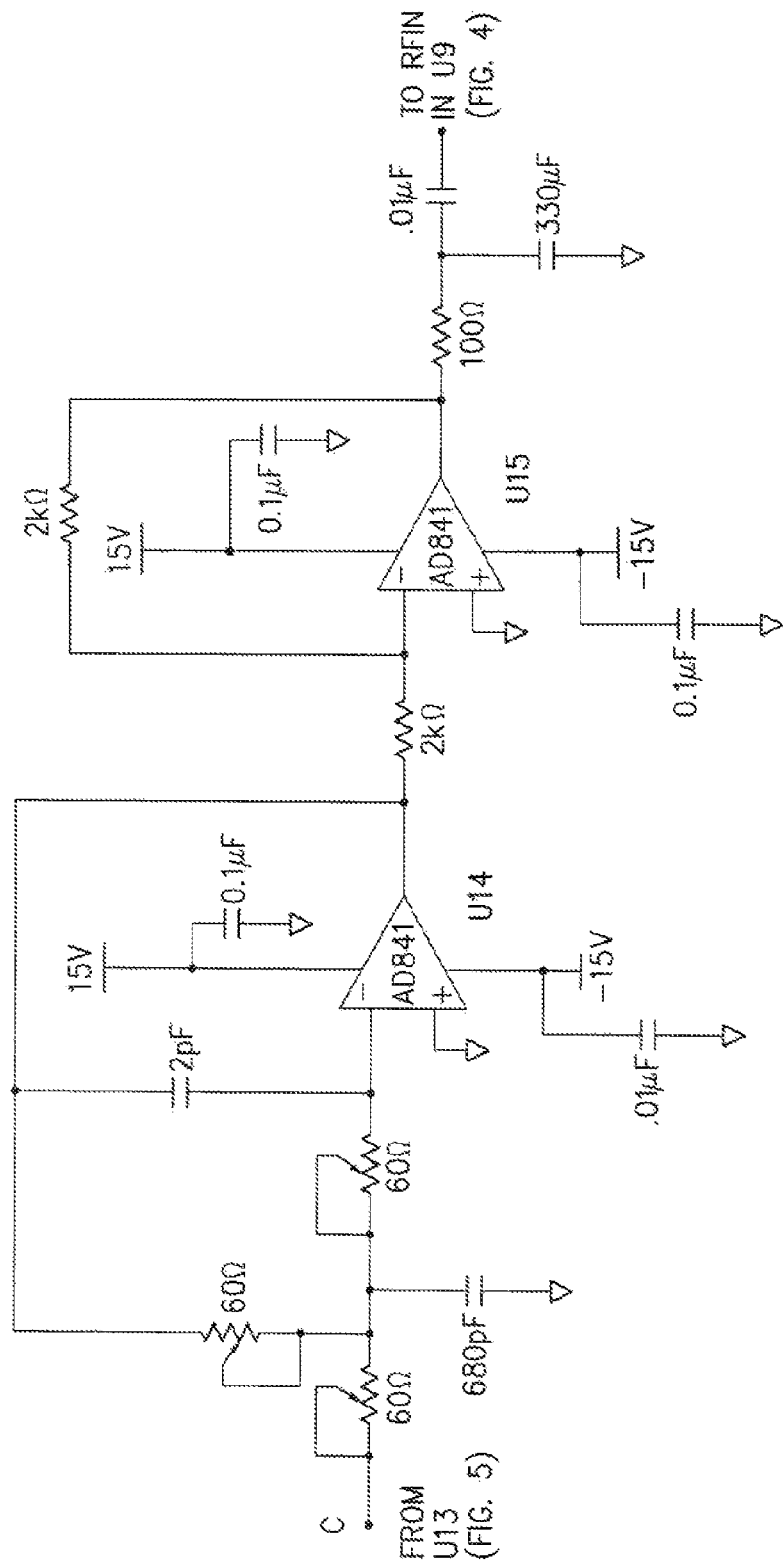
FIG. 6 is a circuit diagram for the circuit linking the comparator U13 to the phase detector RPD1 (U9).

As shown in FIG. 6, the measurement signal is then directed to a filter U14 (an AD841) and converted into a sine wave. The measurement signal is then buffered by U15 (also an AD841) and directed to the phase detector RPD1 (U9). As described supra (and shown in FIG. 4), the phase detector RPD1 (U9) also receives the phase detection signal. The phase detector RPD1 output voltage is designated as PH1. The output voltage PH1 is proportional to the phase angle $\theta 1$.

After Z1, and $\theta 1$ have been measured and calculated for the 1 MHz signal, the real and imaginary parts of the impedance R and X are calculated as $R=|Z| \cos \theta$ and $X=|Z| \sin \theta$. The 1 Mhz value of capacitance C1 of the peanuts P in the sample holder H is given as:

$$C1 = \frac{1}{2\pi f X}$$

Once capacitance C1, phase angle $\theta 1$, and impedance Z1 have been calculated for the 1 MHz signal, the computer L (see FIG. 1) then switches the multiplexer to allow a 5 MHz signal to pass through the sample holder H. The signals are processed through a circuit similar to the 1 MHz circuit but with the range resistor R12 set at a different value. The impedance magnitude Z2 and the phase angle $\theta 2$, and capacitance C2 are determined for the 5 MHz frequency as was done for 1 MHz signal. Similar measurements are made with a 9 MHz signal and impedance Z3, and phase angle $\theta 3$, and capacitance C3 are determined at this frequency.

Moisture Content Determination

The moisture content of a given in-shell peanut sample is determined by calculating phase angle $\theta$, capacitance C, and impedance Z as described supra, at (at least) two frequencies and then substituting the calculated values into a previously-derived moisture content algorithm. The moisture content algorithm was originally derived by the inventors by identifying eight "moisture calibration groups" of in-shell peanut samples. The moisture groups included in-shell peanuts with known moisture levels varying from 6% to 25%. Each of the eight calibration groups was subdivided into 30 sets of samples so that there was a total of 240 samples Each sample was placed in the sample holder, and C, $\theta$ and Z values of each sample were obtained using the CI analyzer (as described supra) at each of at least two frequencies.

The moisture content of each sample was then determined by the standard air-oven method. Multi-linear regression analysis (MLR) was applied to the measurements for each of the 240 samples, with the moisture content of each sample as a Y variable, and the difference in the C, $\theta$ and Z values (at the two frequencies) as the corresponding X variables.

Based on these measurements, the moisture content (MC) regression calibration equation thus derived by the inventors is:

$$MC = A_0 + A_1(C1-C2) + A_2(\theta 1-\theta 2) + A_3(Z1-Z2) + A_4(C1-C2)^2 + A_5(\theta 1-\theta 2)^2 + A_6(Z1-Z2)^2$$

Where $A_0$ to $A_6$ are calibration constants derived through MLR analysis using peanut samples with a known moisture contents.

In summary, as briefly described supra, the moisture content (MC) of a selected in-shell peanut sample is determined by determining the values of C, $\theta$ and Z using the moisture content analyzer C1 at (at least) two frequencies (for example 1 and 5 MHz), and then substituting these values into the calibration equation described supra along with the previously-determined reference values of the calibration constants $A_0$ to $A_6$.

The inventors have verified the performance of the calibration equation described supra based on Standard Error of Calibration and coefficient of determination ($R^2$).

For the foregoing reasons, it is clear that the invention provides an innovative peanut moisture measuring method and apparatus. The invention may be modified in multiple ways and applied in various technological applications. The current invention may be modified and customized as required by a specific operation or application, and the individual components may be modified and defined, as required, to achieve the desired result.

Although the materials of construction are not described, they may include a variety of compositions consistent with the function of the invention. Such variations are not to be regarded as a departure from the spirit and scope of the invention, and all such modifications as would be obvious to one skilled in the art are intended to be included within the scope of the following claims.

What is claimed is:

1. An apparatus for determining the moisture content of in-shell peanuts, the apparatus comprising:
   an oscillator which generates a square wave signal at a predetermined frequency;
   a first filter which receives the signal and shapes the square wave signal into a sine wave signal as an output, wherein the sine wave signal is thereafter split into a measurement signal, a reference signal, and a phase detection signal so that:
   the reference signal is sent through a transformer and rectifier and then measured; and
   the phase detection signal is sent through an attenuator and to a phase detector;
   a multiplexer receives the measurement signal and directs the measurement signal through a selected sample of in-shell peanuts;
   an amplifier comprising a variable range resistor receives the measurement signal, wherein a first portion of the measurement signal from the amplifier is then rectified and measured;
   a comparator receiving a second portion of the measurement signal from the amplifier, wherein the comparator outputs the second portion of the measurement signal as a square wave; and
   a second filter receiving the second portion of the measurement signal converting the second portion of the measurement signal to a sine wave, the second portion of the measurement signal then being directed to the phase detector, the phase detector measuring a phase change between the measurement signal and the phase detection signal;
   wherein moisture content of the in-shell peanuts is calculated based on the measured reference signal, the measurement signal, and the measured phase change.

2. The apparatus of claim 1 wherein an amplitude of the measurement signal, the reference signal, and the phase detection signal is at least 5 volts.

3. The apparatus of claim 1 wherein the oscillator comprises a high frequency oscillator.

4. The apparatus of claim 3 wherein the oscillator comprises an ICM 7209 oscillator or equivalent device.

5. The apparatus of claim 1 wherein the first filter, the amplifier, and the second filter comprise high frequency amplifiers.

6. The apparatus of claim 5, wherein the first filter, the amplifier, and the second filter comprise AD841 operational amplifiers or equivalent devices.

7. The apparatus of claim 1 wherein the comparator comprises an integrated circuit for generating a square wave signal.

8. The apparatus of claim 7 wherein the comparator comprises an integrated circuit capable of outputting a signal with an amplitude of at least 5 volts.

9. The apparatus of claim 8 wherein the comparator comprises an AD9866 device or equivalent device.

10. The apparatus of claim 1 wherein a first data set is generated at a first oscillator frequency, and a second data set is generated at a second oscillator frequency; the first and second data sets being substituted into a semi-empirical equation to determine moisture content of the in-shell peanuts.

11. The apparatus of claim 10 wherein the semi-empirical equation includes constants derived through multi-linear regression analysis.

12. The apparatus of claim 10 wherein the first frequency is 1 MHz.

13. The apparatus of claim 10 wherein the second frequency is 5 MHz.

14. The apparatus of claim 10 wherein the second frequency is 9 MHz.

15. A method for determining the moisture content of in-shell peanuts, the method comprising:
   (a) providing an oscillator in combination with a crystal which generates a square wave signal at a predetermined frequency;
   (b) directing the signal to a first buffer, which buffers the signal;
   (c) directing the signal from the first buffer to a first filter that shapes the signal into a sine wave;
   (d) splitting the sine wave signal from the first filter into a measurement signal, a reference signal, and a phase detection signal;
   (e) sending the reference signal through a transformer and rectifier and measuring the reference signal;
   (f) sending the phase detection signal through an attenuator and into a phase detector;
   (g) sending the measurement signal to a multiplexer and from the multiplexer through a selected sample of in-shell peanuts;
   (h) directing the signal from the multiplexer to an amplifier a variable range resistor, a first portion of the measurement signal being rectified and measured;
   (i) sending a second portion of the measurement signal to a comparator, the comparator outputting the signal as a square wave;
   (j) sending the second portion of the measurement signal from the comparator to a second filter and converting the signal to a sine wave;
   (k) sending the second portion of the signal to the phase detector, the phase detector measuring a phase difference between the second portion of the measurement signal and the phase detection signal; and,
   (l) calculating moisture content of the in-shell peanuts based on the reference signal, the measurement signal, and the phase difference measured by the phase detector.

16. The method of claim 15 wherein the oscillator comprises a high frequency oscillator.

17. The method of claim 16 wherein the oscillator comprises an ICM 7209 oscillator or equivalent device.

18. The method of claim 15 wherein the first buffer, the first filter, the amplifier, and the second filter comprise high frequency amplifiers.

19. The method of claim 18 wherein the first buffer, the first filter, the amplifier, and the second filter comprise AD841 operational amplifiers or equivalent devices.

20. The method of claim 15 wherein the comparator comprises an integrated circuit for generating a square wave signal.

21. The method of claim 20 wherein the comparator comprises an integrated circuit capable of outputting a signal with an amplitude of at least 5 volts.

22. The method of claim 21 wherein the comparator comprises an AD9866 device or equivalent device.

23. The method of claim 15 wherein a first data set is generated at a first oscillator frequency, and a second data set is generated at a second oscillator frequency; the first and second data sets being substituted into a semi-empirical equation to determine moisture content of the in-shell peanuts.

* * * * *